(12) United States Patent
Fischer (10) Patent No.: US 10,959,524 B2
(45) Date of Patent: Mar. 30, 2021

(54) PIECE OF SEATING FURNITURE AND FITTING THEREFOR

(71) Applicant: BEHEERMAATSCHAPPIJ VERMEULEN BEESD B.V., Culemborg (NL)

(72) Inventor: Matthias Fischer, Bratislava (SK)

(73) Assignee: BEHEERMAATSCHAPPIJ VERMEULEN BEESD B.V., Culemborg (NL)

( * ) Notice: Subject to any disclaimer, the term of this patent is extended or adjusted under 35 U.S.C. 154(b) by 58 days.

(21) Appl. No.: 16/325,415

(22) PCT Filed: Jul. 27, 2017

(86) PCT No.: PCT/EP2017/069058
§ 371 (c)(1),
(2) Date: Feb. 14, 2019

(87) PCT Pub. No.: WO2018/033362
PCT Pub. Date: Feb. 22, 2018

(65) Prior Publication Data
US 2019/0208909 A1    Jul. 11, 2019

(30) Foreign Application Priority Data

Aug. 16, 2016  (EP) .................................... 16184390

(51) Int. Cl.
*A47C 1/0355*    (2013.01)
*A47C 1/031*    (2006.01)
(Continued)

(52) U.S. Cl.
CPC ............. *A47C 1/0355* (2013.01); *A47C 1/031* (2013.01); *A47C 1/034* (2013.01); *A61G 5/1067* (2013.01); *A61G 5/14* (2013.01); *A47C 1/0342* (2013.01)

(58) Field of Classification Search
CPC ...... A61G 5/14; A61G 5/1067; A47C 1/0355; A47C 1/0342; A47C 1/0345; A47C 1/031; A47C 1/034
See application file for complete search history.

(56) References Cited

U.S. PATENT DOCUMENTS 4,506,925 A    3/1985  Crum
5,127,705 A    7/1992  Antoine et al.
(Continued)

FOREIGN PATENT DOCUMENTS

DE    20 2015 105 292 U1    11/2015
EP    2 084 992    8/2009
(Continued)

OTHER PUBLICATIONS

International Search Report issued in Application No. PCT/EP2017/069058 dated Sep. 29, 2017 and English translation (5 pages).
(Continued)

*Primary Examiner* — Milton Nelson, Jr.
(74) *Attorney, Agent, or Firm* — Flynn Thiel, P.C.

(57) ABSTRACT

A piece of seating furniture with a base for setting up in a fixed position, a seating element tiltable in relation to the base and having a seating surface, and a leg support element movable in relation to the seating element and having a leg support surface. The leg support element is connected to the seating element via a link gear, wherein the leg support element is movable between a storage position and a use position via the link gear. An electric motor is provided below the seating surface, which acts on the link gear via a push rod. To connect the leg support element to the seating element, the link gear has a pivoting link which, during the transfer of the leg support element from the storage position into the use position, is arranged in part in a slot partially penetrating the leg support surface.

25 Claims, 6 Drawing Sheets

(51) Int. Cl.
*A47C 1/034* (2006.01)
*A61G 5/10* (2006.01)
*A61G 5/14* (2006.01)

(56) References Cited

U.S. PATENT DOCUMENTS

| | | | |
|---|---|---|---|
| 5,857,739 A * | 1/1999 | Smith | A47C 1/03255 |
| | | | 297/68 |
| 6,227,489 B1 * | 5/2001 | Kitamoto | B64D 11/00 |
| | | | 244/118.5 |
| 8,764,112 B2 | 7/2014 | Fischer | |
| 8,985,694 B2 | 3/2015 | Fischer | |
| 9,247,822 B2 | 2/2016 | Fischer | |
| 9,402,479 B1 | 8/2016 | Lin | |
| 2004/0000803 A1 | 1/2004 | Guillot et al. | |
| 2011/0043005 A1 | 2/2011 | Fischer | |
| 2012/0248831 A1 | 10/2012 | Garland | |
| 2013/0257110 A1 | 10/2013 | Fischer | |
| 2016/0270537 A1 | 9/2016 | Marshall et al. | |
| 2017/0071344 A1 * | 3/2017 | Marcantoni | A47C 1/0342 |
| 2017/0238711 A1 * | 8/2017 | Miller | A47C 1/0342 |

FOREIGN PATENT DOCUMENTS

| | | |
|---|---|---|
| EP | 2 609 834 A1 | 7/2013 |
| EP | 2 777 433 A1 | 9/2014 |
| EP | 2 801 293 A1 | 11/2014 |
| WO | 2018/033256 A1 | 2/2018 |

OTHER PUBLICATIONS

Written Opinion issued in Application No. PCT/EP2017/069058 dated Sep. 29, 2017 (6 pages).
European Search Report issued in European Application No. 16184390.9 with English translation of category of cited documents corresponding to the present application dated Jan. 27, 2017 (8 pages).

* cited by examiner

PIECE OF SEATING FURNITURE AND FITTING THEREFOR

FIELD OF USE AND PRIOR ART

The invention relates to a of piece seating furniture, in particular in the form of an armchair, and to a fitting therefor.

Pieces of seating furniture of the type in question and according to the invention have a base for setting up in a fixed position, a seating element which is arranged above the base and so as to be tiltable in relation thereto and has a seating surface, and a leg support element which is attached to the seating element by a link gear and has a leg support surface. The link gear makes it possible to move the leg support element between a storage position under the seating element and a use position in front of the seating element by means of a link which is pivotable about a transverse axis of the furniture.

EP 2609834 A1 discloses a piece of furniture of the type in question, in which an intermediate carrier which is shiftable in relation to a seating element is driven via the link gear. A telescopic rod is attached to said intermediate carrier, and a leg unit is provided at that end of the telescopic rod which is displaceable in relation to the intermediate carrier. The link gear for shifting the intermediate carrier is provided on the outer side of the seating surface.

EP 2084992 A2 discloses another piece of seating furniture, in which a multi-section leg support is provided in a chain-like connection to a seating element. The individual elements are pivoted out successively here, with the motorized configuration also already being proposed.

Other pieces of Seating furniture in the form of armchairs with an electric drive for shifting elements of the piece of seating furniture with respect to one another are also known. However, the construction space for attaching such motors is generally limited and generally makes it necessary to design a piece of seating furniture from the outset as an electrical piece of seating furniture in order to be able to plan the required construction space from the beginning. In addition, electric pieces of seating furniture also have the problem of there being a comparatively high risk of injury when the individual elements and gear parts are moved in relation to one another by motor, in particular since the gears of electrically driven pieces of seating furniture are frequently of such large design that they partly form the outer contours of the piece of seating furniture.

OBJECT AND SOLUTION

It is an object of the invention to provide a piece of seating furniture and a fitting provided therefor, which can be operated electrically and permit a flexible design in respect of attaching to seating furniture of various types.

According to the invention, a piece of seating furniture is proposed for this purpose which has a base for setting up in a fixed position and a seating element which is tiltable in relation to the base and has a seating surface and a carrying structure.

The base can be designed rigidly as a whole and for setting up in a fixed position or can be designed in the form of a two-part base with a foot to be set up in a fixed position and a base portion which is rotatable in relation thereto about a vertical axis of rotation. The base or the rotatable base portion are provided for tiltably attaching the seating element. A particular form of a base makes provision for a "standing-up aid" to be provided between the setting-up surface thereof and the base portion to which the seating element is attached, i.e. a fitting portion, by means of which the seating element and all further elements provided thereon can be jointly raised and inclined slightly forward in order to facilitate standing up from the piece of seating furniture.

The piece of seating furniture furthermore has a leg support element which is movable in relation to the seating element and has a leg support surface and a carrying structure, said leg support element being connected to the seating element by means of a link gear, wherein the leg support element is movable between a storage position under the seating element and a use position in front of the seating element by means of the link gear. A link gear has at least one elongate pivoting link which is the main element for shifting the leg support element in the longitudinal direction of the furniture. The at least one link is attached pivotably on both sides, namely about an axis, which extends in the transverse direction of the furniture, on an attachment portion assigned to the seating element and likewise about an axis, which extends in the transverse direction of the furniture, on an attachment portion assigned to the leg support element. The elongate link preferably pivots by an angle of more than 60°, and therefore the leg-support-element-side pivot axis is shifted at least by the length of the link or the distance between the pivot axes of the link.

An electric motor is provided on the piece of seating furniture according to the invention below the seating surface and acts to drive the link gear. Said electric motor acts on the link gear via a push rod in order thereby to drive the at least one pivoting link in the direction of the use position of the leg support element. The push rod can be the rotor of a linear actuator. However, when a linear actuator is used, a push rod which is separate from the rotor and the sequence of movement of which differs from that of the rotor is preferably also provided.

The leg support element and the leg support surface forming the upper side of the leg support element are of slotted design in the configuration according to the invention. An arrangement which is approximately centered with respect to the seating surface and has at least one slot or a plurality of slots arranged close to one another with an overall width of the slot arrangement <20 cm is therefore provided, the slots making it possible, by the at least one pivoting link entering therein, for the leg support element to be arranged below the seat-element-side pivot axis of the pivoting link in the storage position. As such, the leg support element can remain identically oriented between its storage position under the seating element and its use position in front of the seating element, i.e. in such a manner that the leg support surface is oriented approximately horizontally with an upwardly facing leg support surface (+/45°) at least in the storage position and also in the use position, but preferably also in any intermediate position. This manner of shifting the leg support element with little pivoting leads to a comparatively small movement space necessary for the transfer. In comparison to pieces of seating furniture in which the leg support element is coupled to the seating surface element and therefore a pure pivoting movement, customarily of 75° or more, takes place for the purpose of the extension, the maximum length of the leg support element can be considerably greater in the configuration according to the invention.

The centered arrangement of the at least one pivoting link leads to the risk of pinching, for example, of a finger or of a body part of an animal being highly improbable because of the lack of accessibility. In addition, such a piece of seating furniture can have a fitting which defines the kinematics of the elements and does not have to be adapted to the specific width of a specific piece of seating furniture and which, because of the approximately central arrangement of the pivoting link, also permits an approximately central or only slightly excentric arrangement of the motor, and therefore said motor is difficult to see from the outside. This makes it possible to use the fitting without further adaptations or with only slight adaptations for existing types of pieces of seating furniture and to provide same with an extendable leg support element. In particular, armchairs can even be provided without side parts on both sides of the seating element since the fitting can be of such a small size that it is scarcely visible in such a configuration.

The centered arrangement of the pivoting link and the likewise preferably provided centered arrangement of all of the other gear components has furthermore proven highly advantageous since there are scarcely problems with components bending under load, as may be a concern if the gear has central and clearly excentric partial components.

The carrying structure of the seating element preferably has two mutually parallel cheeks, wherein the latter are in particular connected to each other preferably via a pin or are penetrated by said pin, which defines the main axis for tilting the seating element in relation to the base. Said cheeks are close to each other and are preferably spaced apart from each other by no more than 15 cm. The electric motor mentioned can be arranged in an intermediate space between said cheeks. However, a configuration has proven advantageous in which the electric motor is arranged excentrically and outside the intermediate space formed by the cheeks. In such a configuration, it is of advantage if the electric motor acts on a control member which is mounted rotatably on the cheeks and extends through the intermediate space between the cheeks onto the opposite side in the transverse direction of the furniture where said control member is operatively connected to the tilting gear and/or to the link gear. The carrying structure of the leg support element can also have two cheeks arranged close to each other, wherein the latter can define said slot between them. The at least one pivoting link is preferably mounted on the leg support element side and on the seating element side between the respective cheeks.

It is considered particularly advantageous here if the pivoting links are not arranged directly adjacent to the cheeks, but rather are spaced apart in the transverse direction of the furniture by preferably at least 10 mm, particularly preferably at least 15 mm. A scissors-type effect is thereby prevented here and the risk of injury to children and pets reduced.

In the case of a piece of seating furniture according to the invention, it is provided that the seating element is movable in relation to the base and the leg support element is movable in relation to the seating element. This can be achieved via two separate electric motors. Preferably, however, a tilting gear which can be driven by means of the same electric motor which also serves as drive of the link gear for shifting the leg element is provided for controlling a tilting movement of the seating element. In such a configuration, the electric motor acts on the tilting gear and on the link gear by means of a common control member.

In the case of a piece of seating furniture according to the invention, it is provided that the latter provides at least two, but preferably three different configurations, namely a seating configuration in which the leg support surface is not used and is arranged below the seating surface, and one or two reclining configurations in which the leg support element is extended and is in the use position.

If two reclining configurations are provided, they are preferably a television-viewing position and a sleeping position which primarily differ in that the seating element is pivoted to a differing extent in relation to the base, wherein the use position of the leg support element relative to the seating element is preferably identical in the television-viewing position and the sleeping position.

In particular if a common motor is provided for tilting of the seating element and the extension of the leg support element, it is expedient to configure the tilting gear and/or the link gear in a particular manner in order to coordinate the two movements with each other in time.

The tilting gear can therefore be designed in order, during the movement of the common control member from a starting position into an end position, to bring about a shifting of the seating element in relation to the base, wherein, in at least one movement phase of the control member, the relative position of the seating element with respect to the base remains unchanged.

Alternatively or additionally, the link gear can be designed in order, during the movement of the common control member from a starting position into an end position, to bring about a shifting of the leg support element in relation to the seating element, wherein the link gear is furthermore designed in such a manner that, in at least one movement phase of the control member, the relative position of the leg support element with respect to the seating element remains unchanged.

A movement phase within the context of said temporarily decoupled operative coupling is understood as meaning a phase of at least 10% of a distance of the common control member from the starting position into the end position. The phase is preferably provided to be longer in each case, in particular comprising 20% of the distance. The unchangeability of the relative position of the leg support element with respect to the seating element or of the seating element in relation to the base should be understood as meaning that the respective element is shifted with respect to its specific own overall shifting in relation to its reference element during the transfer from the seating configuration into the reclining configurations only negligibly (<3%) in such a phase.

Slotted guide mechanisms are readily suitable for the technical realization of the decoupling mentioned, as will also be explained below.

The coordination of the relative movements preferably takes place as follows: in a first movement phase, the leg support element is transferred from the storage position into the use position, and therefore the television-viewing configuration is thus already obtained. In this movement phase, the shifting takes place primarily via the link gear. However, it may be expedient that, at the beginning of said phase, tilting via the tilting gear also takes place in order thereby to increase the space under the seating element. This can create the required space under the seating element, along which space the link gear can extend the leg support element, and/or it can be ensured that a sufficient distance remains between the lower side of the leg support element and the floor during the extension such that there is no risk to children's hands or paws of pets.

In a subsequent second movement phase, the seating element is tilted together with the leg support element in relation to the base while the leg support element remains in a fixed position with respect to the seating element, i.e. its relative position with respect to the seating element only negligibly changes, if at all. Said second movement phase ends in the reclining position in which the seating element is maximally tilted and the leg support element takes up its highest position.

Owing to the fact that, in the second movement phase, no more significant shifting takes place between the leg support and the seating element, it is made possible for the seating surface and the leg support surface to be readily aligned with each other in the television-viewing configuration and the sleeping configuration. If, even in this movement phase, a significant relative shifting were to take place between the two elements, the surfaces would not be oriented in alignment in at least one configuration because of the link gear, but would rather form a type of step.

So that the orientation of the leg support in the sleeping position is perceived to be pleasant, it is of advantage if the leg support is oriented horizontally in this position or drops slightly rearward, i.e. is inclined in the direction of the seating surface. So that this is achieved with the leg support element remaining in an unchanged use position with respect to the seating element in the second movement phase, the link gear is designed in such a manner, and optionally adapted to the tilting gear, that the leg support element is oriented toward the end of the first movement phase in such a manner that the leg support surface drops forward.

The link gear preferably has at least one front pivoting link and a rear pivoting link with respect to a longitudinal direction of the furniture which are each attached at one end to a seating-element-side connecting portion so as to be pivotable about first and second pivot axes differing from each other and are each attached at the other end to a leg-support-element-side connecting portion so as to be pivotable about third and fourth pivot axes differing from each other. Said four pivot axes are preferably spaced apart nonuniformly from one another in such a manner that they define a movement path for the leg support element and at the same time bring about a pivoting movement in order in each case to ensure ideal orientations of the leg support surface with respect to the seating surface in the storage position and in the use position.

The connecting portions of the pivoting links are preferably a fixed part of the carrying structures of the seating element and of the leg support element, said carrying structures being fixed in position with respect to the seating surface and the leg support surface. However, alternatively, a relative movability of a connecting portion in relation to the carrying structure of its respective element can in principle also remain, for example in order to be able to pivot the leg support element about a further pivot axis by means of a further gear.

The electric motor is preferably in the form of a linear actuator with a rotor which is extendable in a translatory manner, wherein the rotor is preferably oriented in a main plane of extent (+/10°) of the seating element. The electric motor can be coupled in particular at one end to a carrying structure of the seating element so as to be pivotable about a first motor axis and can be attached at a second end to a control member so as to be pivotable about a second motor axis, and therefore the linear movement is initially deformed into a pivoting movement. A pivotable control member is suitable in particular as a common control member for connecting the tilting gear and the link gear.

In order to transfer the force from the electric motor to the link gear, a push rod is provided which is likewise preferably oriented substantially in a main plane of extent (+/10°) of the seating element. The push rod is coupled at one end on the motor side, in particular by connection to a pivotable control member which is pivoted by the motor. At the other end, the push rod can be coupled pivotably directly to one of the links of the link gear, preferably to the front of the two links, and therefore the rear pivoting link is indirectly moved at the same time because of the front pivoting link.

However, it can instead also act indirectly on the front pivoting link via an additional push link. This additional push link provides the possibility of specifically adapting the angle at which a pivoting torque is transmitted from the push rod to the pivoting link such that the application of force always takes place at an advantageous angle. In addition, the push link also provides a helpful possibility for realizing the desired decoupling of the relative position of the leg support element with respect to the seating element by the continued movement of the push rod being absorbed, as it were, by the push link, but not being transmitted to the leg support element.

In order to realize such a decoupling and/or for coupling force in at an ideal angle, the push rod is preferably guided displaceably on the carrying structure of the seating element. At the same time, the push link is attached to the push rod so as to be pivotable about a first push link axis and is attached to the front pivoting link so as to be pivotable about a second push link axis. The displaceable guide is particularly preferably realized by means of a slotted guide mechanism with a slotted guide track and a slotted guide slider which is movable along the slotted guide track, in particular in the form of a slotted guide roller. The slotted guide track has a slotted guide track portion, the shaping of which is configured in such a manner that the first push link axis substantially describes a circular path in relation to the carrying structure of the seating element and in relation to the second push link axis which is fixed in position for this purpose in this phase. The circular path leads to the push link pivoting about its second push link axis on the side of the pivoting link, but not acting upon the latter with a force. This permits the standard use position of the leg support in both reclining positions.

In order to cover the required travel of the leg support element with a link gear having two pivoting links which are coupled directly on both sides to the carrying structures of the seating element and of the leg support element, the length of the pivoting links and the pivoting angle passed over should be as large as possible, preferably >110°, in particular preferably >120°, with respect to the pivoting link which pivots less far. This means that the pivoting links are greatly stretched when the leg support element is arranged in its use position, and therefore there is the risk of overturning if the fitting is not produced sufficiently precisely.

In order to prevent this, it can be provided that the link gear has a securing strut which is attached to the rear pivoting link so as to be pivotable about a fifth pivot axis and is attached to the front pivoting link so as to be pivotable about a sixth pivot axis. Said pivot axes are offset here from the connecting line between the first and third pivot axis or second and fourth pivot axis in order to have an advantageous position even toward the end of the first movement phase and thereafter and therefore turning over due to excessive force being applied to the leg support element by a lever action is prevented.

Since the first to fourth pivot axes preferably do not form a perfect parallelogram, the distance between the fifth and sixth pivot axes changes during the movement of the link gear. So that this does not lead to blocking of the link gear, it is preferably provided that the securing strut is attached to the rear pivoting link or to the front pivoting link so as to be pivotable and displaceable to a limited extent such that it forces there only to be a minimum distance between the fifth and the sixth pivot axis, but by contrast greater spacing of the pivot axes is not prevented. This can be obtained in particular by connection of the securing-strut by means of an elongate hole.

With regard to the tilting gear, it is considered advantageous if the latter has a main axis which is fixed in position with respect to the seating element and with respect to the base and about which the seating element is tiltable in relation to the base. This creates a very simple and cost-effective type of tiltability. The drive via the common or else a separate electric motor preferably takes place via a control member which is assigned to the tilting gear and is pivotable about a first control member axis and on which a slotted guide slider, preferably in the form of a slotted guide roller, is provided, which, over the course of the pivoting of the control member, is movable along a slotted guide track.

The control member which is preferably rotatable about a control member axis, which is fixed in position with respect to the seating element, because of its guidance along the slotted guide track pivots, over the course of its pivoting, the seating element to a lesser extent therewith. By means of the shaping of the slotted guide track, it is possible here to precisely define in which phase of the overall movement the seating element is intended to be shifted.

If the slotted guide track has a slotted guide track portion which has the shape of a circular portion with respect to the first control member axis, a pivoting movement of the control member in part does not lead to any pivoting of the seating element, and therefore an isolated movement of the leg support element in relation to the seating element can take place in this phase.

The slotted guide track is preferably provided on a slotted guide element which is attached in a tiltproof manner to the base.

A piece of seating furniture according to the invention customarily furthermore has a backrest element with a backrest surface which is preferably attached to the base or to the seating element so as to be pivotable about a backrest axis.

For driving said backrest element, a further electric motor is preferably provided, by means of which the backrest element is pivotable about the backrest axis. This electric motor is activated by a control device of the piece of seating furniture, wherein the activation preferably takes place with the activation of the electric motor or the electric motors, which shifts the seating element and the leg support element. Particularly preferably, the backrest element is pivoted into a flatter position in the second movement phase, in which the piece of seating furniture takes up the sleeping configuration.

As already explained at the beginning, the fitting of a piece of seating furniture according to the invention is suitable for attaching to pieces of seating furniture of differing width and in particular also for armchairs without side cheeks/armrests since the technically complex fitting components and in particular the pivoting links are arranged centrally and require little construction space. Nevertheless, an armchair according to the invention can of course also have armrests. The latter can either be pivotable together with the backrest element about the backrest axis or can be pivoted together with the seating element.

The base mentioned can be designed as a base which is completely rigid per se or else can define an axis of rotation about which a shiftable portion of the base is shiftable in order to attach the seating element in relation to its setting-up portion, for example a plate on the floor.

In a particular configuration of the piece of seating furniture, the latter has a standing-up aid gear between the setting-up portion or an intermediate portion which is rotatable in relation thereto, on the one hand, and the shiftable portion of the base, on the other hand, by means of which standing-up aid gear the shiftable portion is shiftable between a use position and a standing-up position. The gear is provided in order to jointly raise the actual seat, i.e. the seating element, the leg support element and the backrest element, and thus to permit easier standing up.

The gear preferably has two gear links which extend between the setting-up portion or an intermediate portion, which intermediate portion is rotatable in relation thereto, and the shiftable portion and which are pivotable on both sides about different pivot axes. The gear links preferably have an approximately identical length, and therefore the seat is raised approximately parallel. By means of slightly different lengths or by arranging the pivot axes in a shape differing from a parallelogram, it can be achieved that the raising is associated with a slight tilting forward.

The gear links preferably extend rearward from the shiftable portion. Particularly preferably, the two gear links extend from the setting-up portion or the intermediate portion obliquely upward in the use position of the shiftable portion and obliquely downward in the standing-up position.

When the standing-up aid is raised because of the gear links, the seating element together with the leg support approximately describes a circular arc, with the seating element first of all being shifted forward and then rearward again here with respect to the longitudinal direction of the furniture. This has proven highly advantageous in order to permit collision-free raising despite the leg support element located under the seating element.

A bracket, i.e. a rigidly attached torque-coupling-in point away from the connection of the pivot axes, on which an electric motor acts for raising the seat is preferably provided on one of the gear links. Said electric motor is preferably arranged below the seating element, preferably on the opposite side to the excentrically arranged electric motor for shifting the leg support element. This location is indeed preferably used for a backrest electric motor in variants without a standing-up aid. However, said location can also be arranged in the backrest itself.

In the event of a configuration of the piece of seating furniture, in which the seating element is rotatable about a vertical axis in relation to the setting-up portion of the base, an operative connection to the standing-up aid is preferably provided, which ensures that the rotatability is blocked when the standing-up aid gear moves the seat out of the use position.

BRIEF DESCRIPTION OF THE DRAWINGS

Further advantages and aspects of the invention emerge from the claims and from the description below of preferred exemplary embodiments of the invention that are explained below with reference to the figures.

DETAILED DESCRIPTION OF THE EXEMPLARY EMBODIMENTS

Figure 1A:
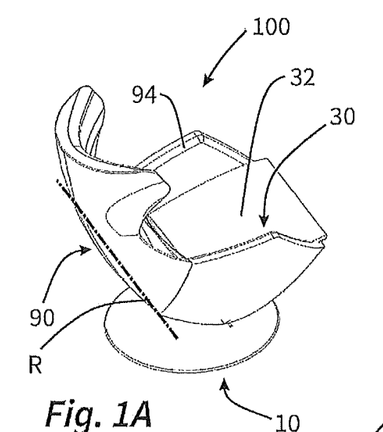
FIGS. 1A to 1C show an example of a piece of seating furniture according to the invention in three configurations.
Figure 1B:
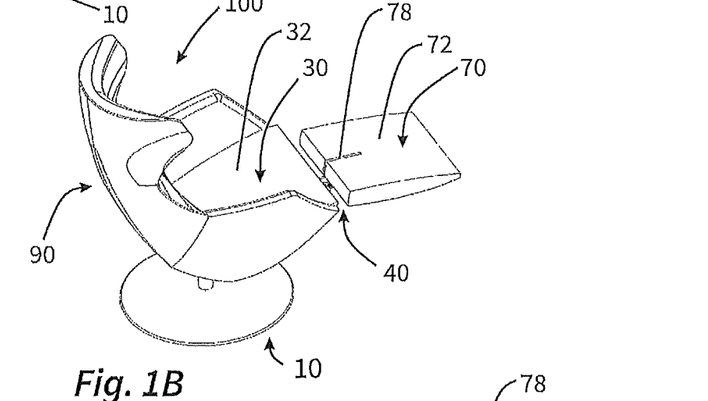
Figure 1C:
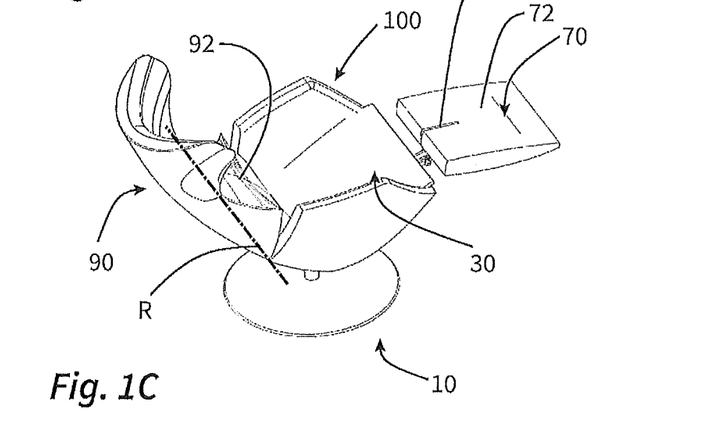

FIGS. 1A and 1C show by way of example a piece of seating furniture according to the invention which can be moved between three possible configurations in which its elements are each arranged in a different position and orientation with respect to a base 10. FIG. 1A shows a seating configuration. FIG. 1B shows a first reclining configuration with an extended leg support element 70, what is referred to as the television-viewing configuration. FIG. 1C shows a second reclining configuration after pivoting of the seating element 30 has continued and the backrest element 90 with a backrest surface 92 is oriented flatter. This is what is referred to as the sleeping configuration.

In the position of FIG. 1A, the seating configuration, upright seating on the seating surface 32 of the seating element 30 is possible. From here, the piece of seating furniture 100 can be moved into the first reclining configuration by the leg support element 70 being shifted from its storage position of FIG. 1A into its use position in front of the seating element 30 and the seating surface 32. Use is made here of a link gear 40 which will be explained in more detail below and which has pivoting links 46, 48 which, in the storage position of FIG. 1, were arranged in the slot 78, visible in FIG. 1B, of the leg support element 70. The latter is also provided for this purpose with a central slot 79 in the region of the fitting.

Starting from the first reclining configuration of FIG. 1B, the piece of seating furniture 100 can be moved into the second reclining configuration of FIG. 1C. The seating element 30 and the seating surface 32 remain fixed in position here relative to the leg support element 70 and the leg support surface 72. However, the seating element 30 and the leg support element 70 continue to pivot together with each other, and therefore the seating surface is arranged in a vertical respect below the leg support surface 72. In this phase, the backrest element 90 is also moved into a flatter orientation by means of a separate electric motor.

FIGS. 2A and 2B to 5A and 5B illustrate the changes mentioned in the configurations with reference to a sectioned lateral illustration and an unsectioned illustration of the fitting 110 of the piece of seating furniture 100 in each case. The backrest element 90 and the corresponding fitting parts are not illustrated in these illustrations.

Figure 2A:
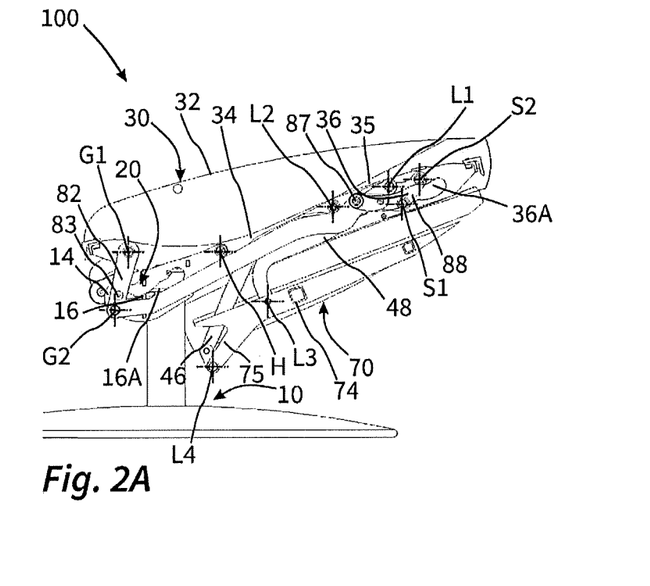
FIGS. 2A and 2B show the piece of seating furniture and the furniture fitting thereof in a seating configuration of the piece of seating furniture.
Figure 2B:
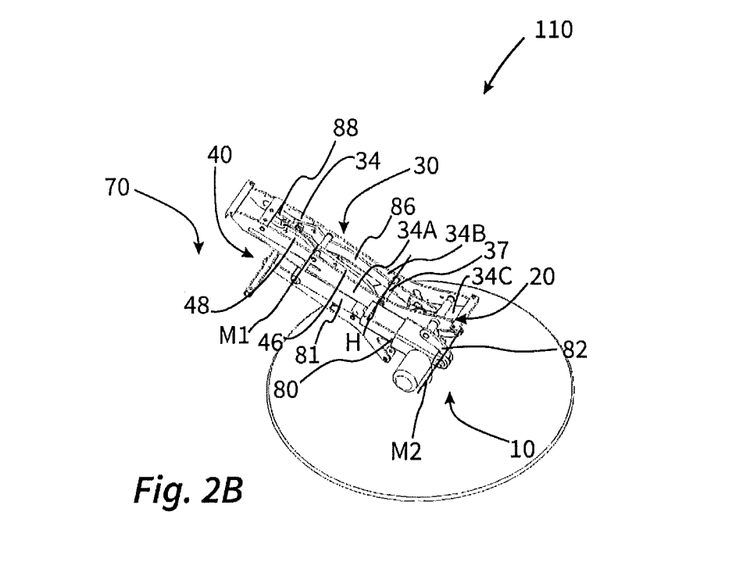

FIGS. 2A and 2B correspond to the configuration of FIG. 1A, i.e. the seating configuration. In this configuration, the leg support element 70 is arranged below the seating element 30 and especially below the seating surface 32 thereof. The leg support element 70 is oriented here in a manner rising forward in order thereby to be able to be placed closely against the lower side of the seating element 30.

The leg support element 70 is connected to the seating element 30 via respective carrying structures 34, 74. The latter respectively have connecting portions 35, 75 to which a rear and a front pivoting link 46, 48 of the link gear 40 are coupled so as to be pivotable about pivot axes L1, L2 on the side of the seating element 30. The pivoting links 46, 48 are coupled at their respective opposite ends to the connecting portion 75 of the carrying structure 74 of the leg support element 70 so as to be pivotable about the pivot axes L3, L4. The pivot axes L1, L2, L3, L4 and the respective distances between them define the movement path of the leg support element 70 relative to the seating element, wherein it is ensured by differences in the distances L1-L3, L2-L4, L1-L2, L3-L4 that the leg support element 70 is inevitably also pivoted during the shifting along said path.

At the rear end of the seating element 30, the latter is coupled pivotably to a base 10, which is provided for setting up in a fixed position, specifically about the main axis H, defined by a pin 37. Alternatively, a link gear similar to the link gear 40 can also be provided here.

For the transfer of the piece of seating furniture 100 into the configurations illustrated in FIGS. 1B and 1C, a series of motor elements and gear elements are provided.

The piece of seating furniture 100 has a common electric motor 80 in the form of a linear actuator for shifting the seating element 30 in relation to the base 10, on the one hand, and for shifting the leg support element 70 in relation to the seating element 30, on the other hand. The electric motor 80 has an extendable rotor 81 which is attached on the end side to the carrying structure 34 of the seating element 30 so as to be pivotable about a first motor pivot axis M1. The opposite end of the electric motor 80 is defined by the second motor pivot axis M2 at which the electric motor 80 is connected pivotably to a control member 82. This control member 82 is attached rotatably to two cheeks 34A, 34B of the carrying structure 34 that define an intermediate space 34C in which in particular the pivoting links 46, 48 are arranged.

The control member 82 has two extension arms on both sides of the cheeks 34A, 34B. The extension arm on the side of the electric motor 80 is provided for connection of the motor. The opposite extension arm, which can be seen in FIG. 2A, serves for connecting both a tilting gear 20 for tilting the seating element 30 and the link gear 40 which has already been mentioned and the main components of which are the front and the rear pivoting links 48, 46. The extension arm of the control member 82 on the side opposite the electric motor 80 has a slotted guide slider 83 in the form of a slotted guide roller which is arranged in a slotted guide track 16, which belongs to the base, of a slotted guide element 14. The control member 82 is pivotable as a whole, i.e. together with the extension arms mentioned, on the seating element 30 about the control member axis G1. A push rod 86 is attached to the opposite distal end of the motor-averted extension arm of the control member 82 and serves for transmitting force from the control member 82 to the link gear 40. For this purpose, the push rod 86 is guided on the front side opposite the control member axis G2 in a base-side slotted guide track 36 by means of a slotted guide slider 87.

At the distal end of the push rod 86, the latter has a push link 88 which is connected thereto, is coupled pivotably about the push link axis S1 and is coupled at its opposite end to the front pivoting link 48 so as to be pivotable about the push link axis S2. As a result, the force of the electric motor 80 can be used in order to pivot out the leg support element 70 by means of the front pivoting link 48 counterclockwise with respect to FIG. 2A. Owing to the fact that the push rod 86 is not coupled directly to the front pivoting link 48, an application of force can take place at an advantageous angle, which is of relevance in particular because of the large overall pivoting angles of the pivoting links 46, 48. Furthermore, the basis is thereby also created to the effect that, during the transfer from the first reclining configuration into the second reclining configuration, a relative movement no longer takes place between the leg support element and the seating element or said relative movement is provided at least only to a very small extent.

Figure 3A:
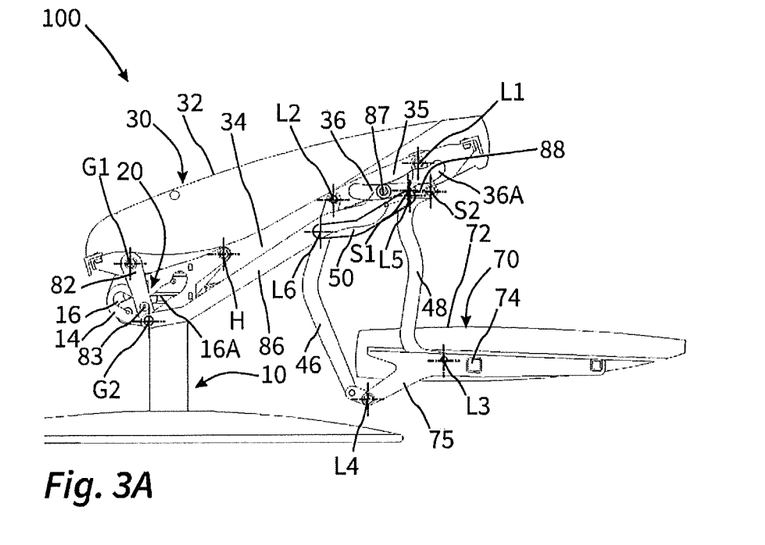
FIGS. 3A and 3B show the piece of seating furniture and the furniture fitting thereof in an intermediate state during the transfer into a first reclining configuration, namely the television-viewing configuration.
Figure 3B:
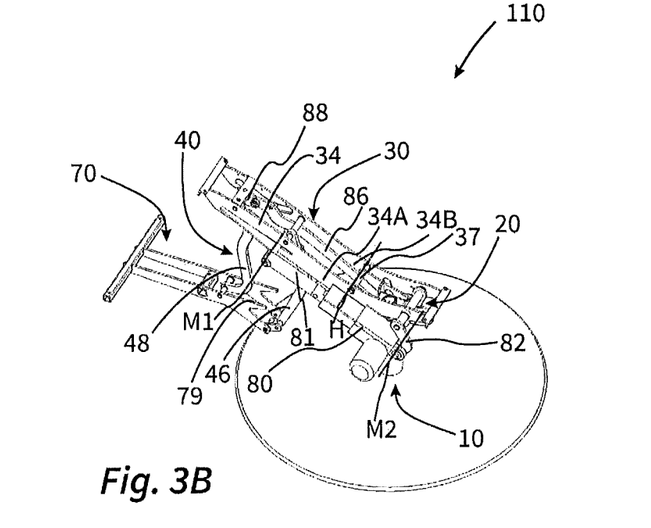

If, starting from the configuration of FIGS. 1A and also 2A and 2B, the electric motor is activated, an intermediate situation corresponding to FIGS. 3A and 3B arises on the path into the first reclining configuration. It can be seen that the pivoting movement of the control member 82, which has been caused by extension of the rotor 81, has influenced the position of the elements of the piece of seating furniture 100 in two respects.

Firstly, the push rod 86 has been shifted forward in the direction of the front seating edge, which, with the aid of the push link 88, has led to the pivoting link 48 and indirectly also the pivoting link 46 being pivoted out. By means of the different distance between the pivot axes L1, L2 and L3, L4 and/or by means of the different lengths of the pivoting links 46, 48, in the intermediate state of FIG. 3A the leg support element is no longer oriented rising forward, but rather is oriented virtually horizontally.

So that the leg support element 70 can be securely extended at all without temporary contact with the floor, a slight pivoting of the seating element 30 counterclockwise with respect to FIG. 3A has also taken place by the slotted guide slider 83 having been shifted along the slotted guide track 16 and the triangle consisting of the axes G1, H and the slotted guide slider 83 that defines the pivoting angle of the seating element 30 having changed. The front part of the seating element 30 has thereby been slightly raised, and therefore, even in this state with the leg support element 70 lowered to the maximum, no collision with the floor takes place.

It can be seen in the state of FIGS. 3A, 3B that the pivoting links 46, 48 are connected to each other by a further connecting strut, the securing strut 50 shown by dashed lines. This strut is attached to the two pivoting links 46, 48 so as to be pivotable about pivot axes L5, L6, but has some play in relation to one of the two, which can be achieved, for example, via an elongate hole. As the extension of the leg support element and the associated severe stretching of the pivoting links 46, 48 continues, the securing link is intended to ensure that the leg support element 70 does not overturn, as is explained below.

Figure 4A:
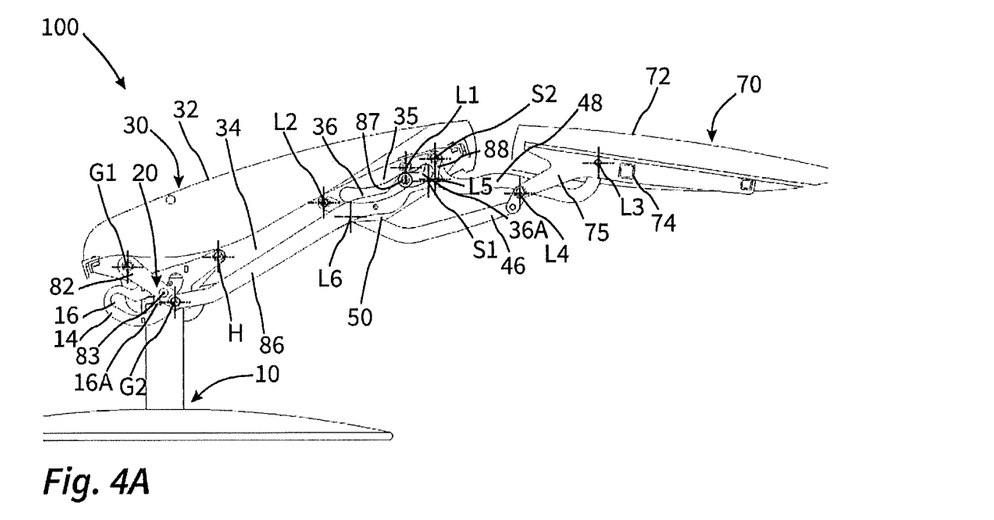
FIGS. 4A and 4B show the piece of seating furniture and the furniture fitting thereof in the television-viewing configuration.
Figure 4B:
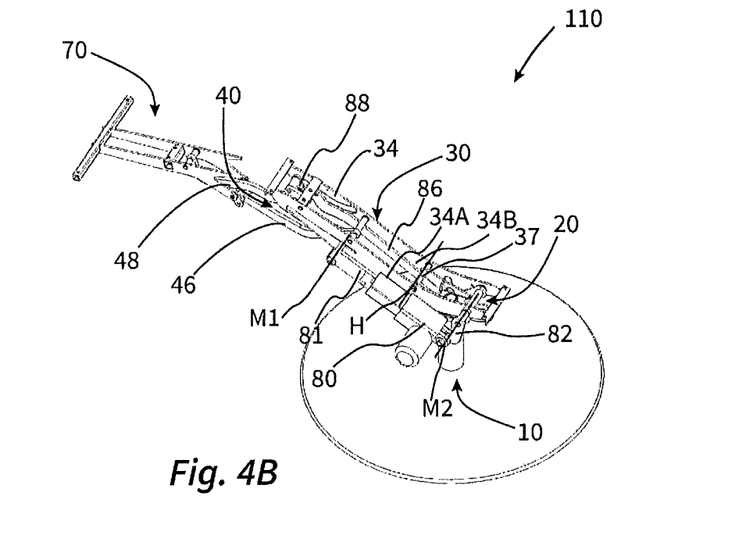

As the movement continues, the first reclining configuration is reached, as illustrated in FIGS. 4A and 4B and also in FIG. 2B. The seating element 30 has remained in a fixed position between the positions of FIGS. 3A, 3B and 4A, 4B, 2B. This has been achieved by a central slotted guide track portion 16A of the slotted guide track 16, which portion constitutes a circular portion form with respect to the control member axis G1. Said slotted guide track portion 16A makes it possible that, in this phase between FIGS. 3A, 3B and 4A, 4B, the control member 82 pivots further, but this does not influence the seating element 30.

By contrast, during the transfer into the state of FIGS. 4A, 4B, 2B, the leg support element 70 has passed into its relative end position with respect to the seating element 30. In this state, the seating surface 32 and the leg support surface 72 are substantially aligned with each other. An annoying step therefore does not arise between them. In this configuration, the leg support surface 72 is oriented dropping slightly forward, which is perceived as pleasant in the typical television-viewing situation.

In the relative position of the leg support element 70 in relation to the seating element 30, as arises after FIGS. 4A, 4B, the square which is formed by the pivot axes L1, L2, L3, L4 is very flat, and therefore the pivot axes are virtually aligned with one another. There is thereby the risk that, when a high force is applied to the leg support element, the pivot axis L4 will fold upward such that the pivoting links 46, 48 cross each other. However, even when the fitting is imprecisely manufactured, this is prevented by the securing strut 50 which prevents such a folding over on account of the arrangement of its pivot axes L5, L6 in a manner offset with respect to the respective connecting lines L1-L3, L2-L4.

Figure 5A:
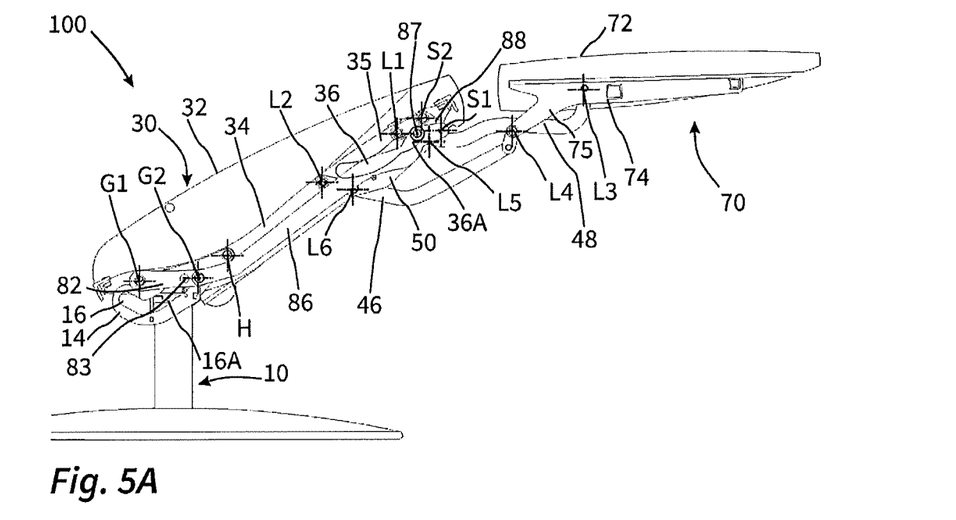
FIGS. 5A and 5B show the piece of seating furniture and the furniture fitting thereof in a second reclining configuration, the sleeping configuration.
Figure 5B:
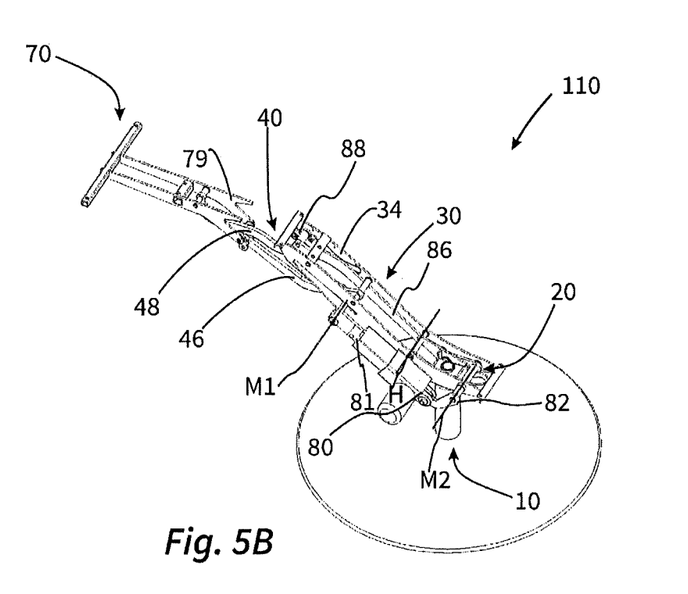

As operation of the electric motor 80 continues, the state of FIGS. 5A, 5B and 1C arises, which is the second reclining configuration. During the transition from the first reclining configuration of FIGS. 4A, 4B to the second reclining configuration of FIGS. 5A, 5B, a relative shifting of the leg support element 70 with respect to the seating element 30 does not occur. This is because, in a final slotted guide track portion 36A of the slotted guide track 36, the latter has a shaping which leads to the push link axis S1 passing through a circular arc movement about the push link axis S2. However, an application of force via the push link 88 to the push link axis S2 no longer takes place and therefore nor does any shifting of the leg support element 70 in relation to the seating element 30.

However, at the tilting gear 20, in said final phase, the slotted guide slider 83 has left the decoupling slotted guide track portion 16A, and therefore, in said final phase, the pivoting movement of the control member 82 causes tilting of the seating element and therefore also of the leg support element 70, which turns out to be very pronounced because of the pronounced curvature in this end portion of the slotted guide track 16. In said final phase, the seating element 30 is pivoted once again approximately by 10° to 15°.

Figures 6A, 6B:
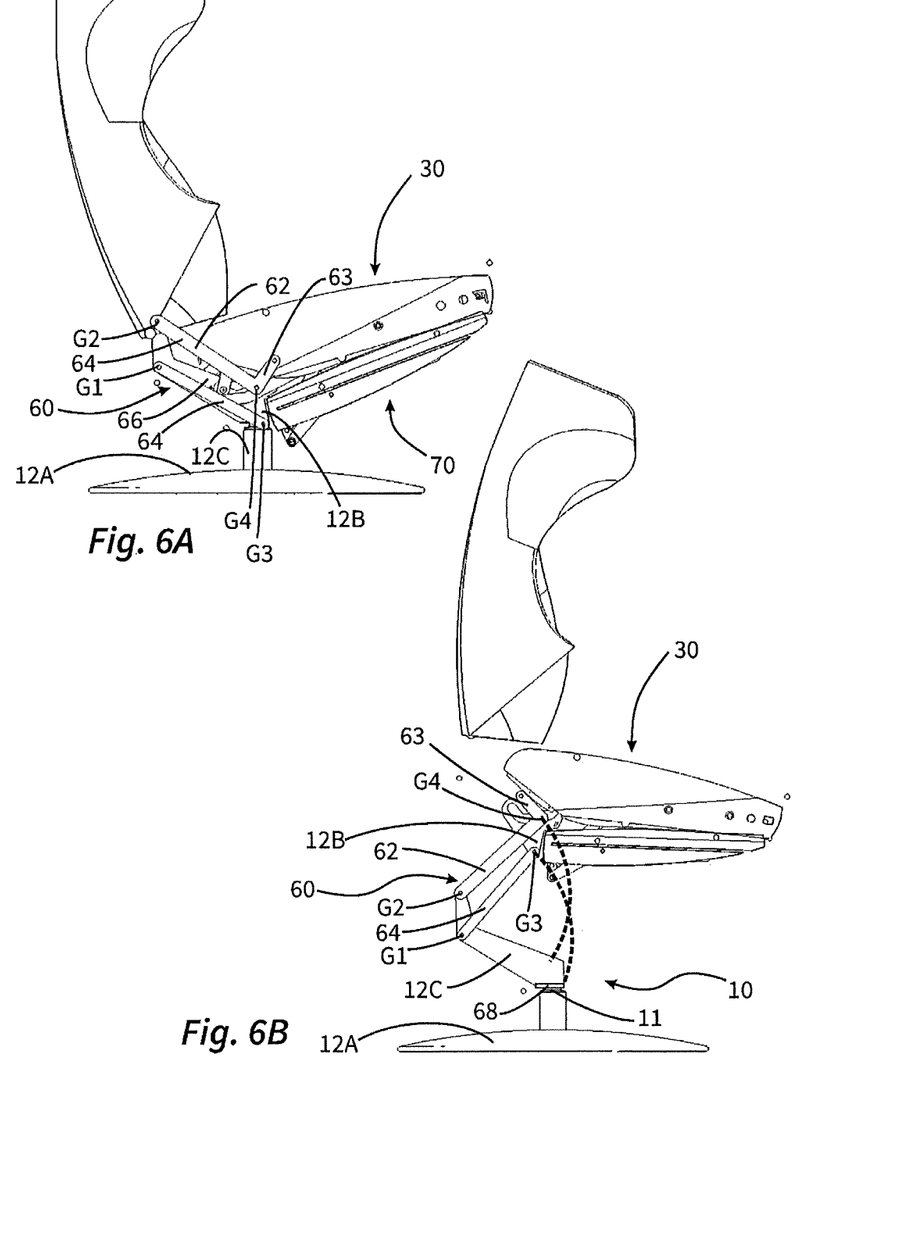
FIGS. 6A and 6B show a variant of the piece of seating furniture with a standing-up aid function.

The configuration according to the invention provides an electrified piece of seating furniture which, on account of the central arrangement of most of the mechanical elements and in particular of the pivoting links during operation, is associated with only a very small risk of injury and makes only small changes necessary to existing models of pieces of seating furniture in order to be able to provide them with a leg support element in an electrified configuration. In particular, the invention also provides measures for keeping the required construction space of a fitting according to the invention small by the fact that only one motor is responsible for the two movements, wherein an expedient sequence of movement can nevertheless be brought about by temporary decoupling. FIGS. 6A and 6B show a variant of the piece of seating furniture with a standing-up aid function. The piece of seating furniture substantially corresponds in a technical respect to that which has been explained. Relevant differences arise only in respect of the base 10.

In this configuration, the base 10 has a floor-side setting-up portion 12A to which an intermediate portion 12C having a bent shaping is attached so as to be rotatable about a vertical axis of rotation. The standing-up aid gear 60 is provided between said intermediate portion 12C and a shiftable portion 12B which is identical to the slotted guide element 14. Said standing-up aid gear comprises two gear links 62, 64 which are pivotable about pivot axes G1, G2, G3, G4 on the intermediate portion 12C and on the shiftable portion 12B. The gear link 62 is formed at one end with a bracket 63 on which a second electric motor acts in a manner not illustrated, said electric motor being arranged approximately in a mirror-inverted manner with respect to the described electric motor 80 on the opposite side with respect to the transverse direction of the furniture.

FIG. 6A shows the use state in which the piece of seating furniture can be used in the described manner. The gear links 62, 64 extend forward and downward from the intermediate portion 12C. The seating element rests on a pressure surface 68 on the intermediate portion 12C, by application of force to which a rotary brake between the intermediate portion 12C and the floor-side setting-up portion 12A is released so that the seat is rotatable.

If the electric motor now activates the standing-up aid function, said electric motor couples a torque into the gear link 62, and therefore the shiftable portion 12B is raised and, because of the arrangement of the pivot axes G1, G2, G3, G4, is also slightly tilted forward. The movement of the pivot axes G3, G4 and of the shiftable portion 12B takes place here along the path illustrated by dashed lines in FIG. 6B. It is apparent that the seating element 30 is shifted together with the leg support element 70 along a circular path.

At the beginning of the raising of the seating element 30, the latter is also raised by the pressure surface 68 which has up to now permitted the release of the rotation of the intermediate portion 12C in relation to the floor-side setting-up portion 12A. Rotational blocking therefore arises, by means of which standing up is facilitated.

The invention claimed is:

1. A piece of seating furniture comprising:
a base for setting up in a fixed position;
a seating element which is tiltable in relation to the base and having a seating surface and a carrying structure;
a leg support element which is movable in relation to the seating element and having a leg support surface and a carrying structure, the leg support element being connected to the seating element by a link gear, and the leg support element being movable between a storage position under the seating element and a use position in front of the seating element by the link gear; and
an electric motor below the seating surface, the electric motor acting on the link gear via a push rod;
wherein to connect the leg support element to the seating element, the link gear has at least one pivoting link which, during the transfer of the leg support element from the storage position into the use position, is arranged in part in a slot partially penetrating the leg support surface.

2. The piece of seating furniture as claimed in claim 1, wherein
the electric motor is in the form of a linear motor with an extendable rotor, and the rotor is oriented in a main plane of extent of the seating element.

3. The piece of seating furniture as claimed in claim 1, wherein
the piece of seating furniture has a backrest element with a backrest surface, said backrest element being attached to the base or to the seating element so as to be pivotable about a backrest axis.

4. The piece of seating furniture as claimed in claim 1, wherein a movement of the seating element in relation to the base is coupled to a movement of the leg support element in relation to the seating element such that
in a first movement phase, the leg support element is transferred from the storage position into the use position, and
in a subsequent second movement phase, the seating element is tilted together with the leg support element in relation to the base while the leg support element remains in a fixed position with respect to the seating element.

5. The piece of seating furniture as claimed in claim 4, wherein
in a position toward an end of the first movement phase and before a beginning of the second movement phase, the leg support element is oriented such a that the leg support surface drops forward.

6. The piece of seating furniture as claimed in claim 5, wherein
in a position toward an end of the second movement phase, the leg support element is oriented such a that the leg support surface is oriented horizontally or drops rearward.

7. The piece of seating furniture as claimed in claim 1, wherein
the link gear has at least one front pivoting link and a rear pivoting link which are each attached at one end to a seating-element-side connecting portion so as to be pivotable about first and second pivot axes differing from each other and are each attached at the other end to a leg-support-element-side connecting portion so as to be pivotable about third and fourth pivot axes differing from each other.

8. The piece of seating furniture as claimed in claim 7, wherein
the seating-element-side connecting portion is formed by a part of the carrying structure of the seating element, the carrying structure of the seating element being provided in a fixed position with respect to the seating surface; and/or
the leg-support-element-side connecting portion is formed by a part of the carrying structure of the leg support element, the carrying structure of the leg support element being provided in a fixed position with respect to the leg support surface.

9. The piece of seating furniture as claimed in claim 7, wherein
the push rod, via which the electric motor acts on the link gear, is connected to the link gear such that the push rod acts on the front pivoting link directly or via an additional push link, and the rear pivoting link is indirectly moved at the same time due to movement of the front pivoting link.

10. The piece of seating furniture as claimed in claim 9, wherein
the push rod is guided displaceably on the carrying structure of the seating element, and
the additional push link is attached to the push rod so as to be pivotable about a first push link axis and the additional push link is attached to the front pivoting link so as to be pivotable about a second push link axis.

11. The piece of seating furniture as claimed in claim 10, wherein
the push rod is guided by a slotted guide mechanism with a slotted guide track and a slotted guide slider which is movable along the slotted guide track.

12. The piece of seating furniture as claimed in claim 11, wherein
the slotted guide track has a slotted guide track portion, the shaping of which is configured such that the first push link axis describes a circular path in relation to the carrying structure of the seating element and in relation to the second push link axis.

13. The piece of seating furniture as claimed in claim 7, wherein the link gear has a securing strut which is attached to the rear pivoting link so as to be pivotable about a fifth pivot axis and is attached to the front pivoting link so as to be pivotable about a sixth pivot axis, a connecting line between the first and the third pivot axis encloses an angle of at least 15° with a connecting line between the first and the fifth pivot axis, and a connecting line between the second and the fourth pivot axis encloses an angle of at least 15° with a connecting line between the second and the sixth pivot axis.

14. The piece of seating furniture as claimed in claim 13, wherein the securing strut is attached to the rear pivoting link or to the front pivoting link so as to be pivotable and displaceable to a limited extent such that the securing strut forces there to be a minimum distance between the fifth and the sixth pivot axis.

15. The piece of seating furniture as claimed in claim 1, wherein the base has a setting-up portion and a shiftable portion, and a standing-up aid gear is provided between the setting-up portion, or an intermediate portion which is rotatable in relation thereto, and the shiftable portion, by which standing-up aid gear the shiftable portion is shiftable between a use position and a standing-up position, and the standing-up aid gear has two gear links which extend rearward from the shiftable portion.

16. The piece of seating furniture as claimed in claim 15, wherein the two gear links extend from the setting-up portion or the intermediate portion obliquely upward in the use position of the shiftable portion and obliquely downward in the standing-up position.

17. The piece of seating furniture as claimed in claim 1, further including a tilting gear which can be driven by the electric motor for controlling a tilting movement of the seating element, and the electric motor acts on the tilting gear and the link gear with a control member.

18. The piece of seating furniture as claimed in claim 17, wherein:

the tilting gear is designed to bring about a shifting of the seating element in relation to the base during a movement of the control member from a starting position into an end position, and the tilting gear is furthermore designed such that, in at least one movement phase of the control member, a relative position of the seating element with respect to the base remains unchanged; and/or the link gear is designed to bring about a shifting of the leg support element in relation to the seating element during a movement of the control member from a starting position into an end position, and the link gear is furthermore designed such that, in at least one movement phase of the control member, a relative position of the leg support element with respect to the seating element remains unchanged.

19. The piece of seating furniture as claimed in claim 17, wherein the tilting gear has a main axis which is fixed in position with respect to the seating element and with respect to the base and about which the seating element is tiltable in relation to the base, and the tilting gear is assigned to the control member which can be pivoted about a first control member axis by the electric motor and on which a slotted guide slider is provided which, over the course of the pivoting of the control member, is movable along a slotted guide track such that the seating element is thereby tilted about the main axis.

20. The piece of seating furniture as claimed in claim 19, wherein the slotted guide track has a slotted guide track portion which has the shape of a circular portion with respect to the first control member axis.

21. The piece of seating furniture as claimed in claim 19, wherein the slotted guide track is provided on a slotted guide element, which is provided in a tilt-proof manner on the base, and the first control member axis is provided in a fixed position with respect to the seating element.

22. The piece of seating furniture as claimed in claim 17, wherein the electric motor comprises a length-changeable linear motor which is coupled at one end to the carrying structure of the seating element so as to be pivotable about a first motor pivot axis and is coupled at a second end to the control member so as to be pivotable about a second motor pivot axis.

23. The piece of seating furniture as claimed in claim 22, wherein the carrying structure of the seating element has two mutually parallel cheeks which are connected or penetrated by a pin which defines a main axis for tilting the seating element in relation to the base.

24. The piece of seating furniture as claimed in claim 23, wherein the electric motor is arranged in an intermediate space between cheeks of the carrying structure of the seating element, or the electric motor is arranged excentrically and outside the intermediate space formed by the cheeks.

25. A fitting for a piece of seating furniture, the fitting comprising:

a base for setting up in a fixed position;

a carrying structure which is rigid for carrying a seating element of the piece of seating furniture;

a carrying structure which is rigid for carrying a leg support element of the piece of seating furniture, which leg support element is connected movably in relation to the carrying structure of the seating element, the carrying structure of the leg support element being connected to the carrying structure of the seating element by a link gear, and the carrying structure of the leg support element is movable between a storage position under the carrying structure of the seating element and a use position in front of the carrying structure of the seating element by the link gear; and an electric motor on the carrying structure of the seating element, the electric motor acting on the link gear via a push rod;

wherein to connect the carrying structure of the leg support element to the carrying structure of the seating element, the link gear has at least one pivoting link which, during transfer of the leg support element from the storage position into the use position, is arranged in part in a slot penetrating the carrying structure of the leg support element.

* * * * *